US006773912B1

(12) United States Patent
Tagg et al.

(10) Patent No.: US 6,773,912 B1
(45) Date of Patent: Aug. 10, 2004

(54) LANTIBIOTIC

(75) Inventors: John Robert Tagg, Dunedin (NZ); Karen Patricia Dierksen, Corvallis, OR (US); Mathew Upton, Manchester (GB)

(73) Assignees: University of Otago, Dunedin (NZ); Blis Technologies Limited, Dunedin (NZ)

( * ) Notice: Subject to any disclaimer, the term of this patent is extended or adjusted under 35 U.S.C. 154(b) by 0 days.

(21) Appl. No.: 09/913,763
(22) PCT Filed: Oct. 12, 2000
(86) PCT No.: PCT/NZ00/00197
§ 371 (c)(1), (2), (4) Date: Dec. 21, 2001
(87) PCT Pub. No.: WO01/27143
PCT Pub. Date: Apr. 19, 2001

(30) Foreign Application Priority Data

Oct. 12, 1999 (NZ) ................................. 500261

(51) Int. Cl.$^7$ ........................... C12N 1/20; A01N 63/00
(52) U.S. Cl. .................................. 435/253.4; 424/93.44
(58) Field of Search ..................... 435/253.4; 424/93.44

(56) References Cited

U.S. PATENT DOCUMENTS

| | | | |
|---|---|---|---|
| 3,925,160 A | | 12/1975 | Sanders, Jr. et al. |
| 4,710,379 A | * | 12/1987 | Kawai et al. |
| 5,378,459 A | | 1/1995 | Grahn et al. |
| 5,468,479 A | * | 11/1995 | Matsushiro |
| 5,872,001 A | | 2/1999 | Caufield et al. |

FOREIGN PATENT DOCUMENTS

| CA | 2268744 | 4/1998 |
|---|---|---|

OTHER PUBLICATIONS

Caufield et al., Computer Sequence Search Display, WO 9817685, 1998.*

Piard et al., "Structure, Organization, and Expression of the lct Gene for Lacticin 481, a Novel Lantibiotic Produced by Lactococcus lactis"; J. Biol. Chem. 1993 Aug. 5; 268(22):16361–68.

John Tagg, "Prevention–Still Better Than a Cure", Microbiology Australia, Jul. 1996, pp. 18–20.

Kalmokoff, et al., "Evidence for Production of a New Lantibiotic (Butyrivibriocin OR79A) by the Ruminal Anaerobe Butyrivibrio fibrisolvens OR79: Characterization of the Structural Gene Encoding Butyrivibriocin OR79A", Applied and Environmental Microbiology, vol. 65, No. 5, May 1999, pp. 2128–2135.

Ross, et al., "Isolation and Characterization of the Lantibiotic Salivaricin A and Its Structural Gene salA from Streptococcus salivarius 20P3", Applied and Environmental Microbiology, vol. 59, No. 7, Jul. 1993, pp. 2014–2021.

* cited by examiner

Primary Examiner—Michael Meller
(74) Attorney, Agent, or Firm—Frommer Lawrence & Haug LLP

(57) ABSTRACT

This invention provides an antibacterial protein, Salivaricin B. Salivaricin B is bacteriocidal with respect to, inter alia, S. pyogenes and therefore has numerous therapeutic applications. These applications include, but are not limited to, forming part of therapeutic formulations for use in treating or preventing streptococcal infections of the throat.

25 Claims, 3 Drawing Sheets

| 1  | TTG | ACT | CTT | GAA | GAA | CTT | GAT | AAC | GTT | CTT | GGT | GCT | GGT |    |
|----|-----|-----|-----|-----|-----|-----|-----|-----|-----|-----|-----|-----|-----|----|
|    | Leu | Thr | Leu | Glu | Glu | Leu | Asp | Asn | Val | Leu | Gly | Ala | Gly | 13 |
|    | -12 |     |     |     |     |     |     |     |     |     |     | -1  | +1  |    |

| 40 | GGT | GGA | GTA | ATC | CAA | ACC | ATT | TCA | CAC | GAA | TGT | CGT | ATG |    |
|----|-----|-----|-----|-----|-----|-----|-----|-----|-----|-----|-----|-----|-----|----|
|    | Gly | Gly | Val | Ile | Gln | Thr | Ile | Ser | His | Glu | Cys | Arg | Met | 26 |

| 80 | AAC | TCA | TGG | CAG | TTC | TTG | TTT | ACT | TGT | TGC | TCT | TAA |    |
|----|-----|-----|-----|-----|-----|-----|-----|-----|-----|-----|-----|-----|----|
|    | Asn | Ser | Trp | Gln | Phe | Leu | Phe | Thr | Cys | Cys | Ser | •   | 37 |
|    |     |     |     |     |     |     |     |     |     |     | +25 |     |    |

Figure 2

| 1 | ATG | ATT | GCC | ATG | AAA | AAC | TCA | AAA | GAT | ATT | TTG | AAC | AAT | |
|---|---|---|---|---|---|---|---|---|---|---|---|---|---|---|
| | Met | Ile | Ala | Met | Lys | Asn | Ser | Lys | Asp | Ile | Leu | Asn | Asn | 13 |
| | -29 | | | | | | | -20 | | | | | | |

| 40 | GCT | ATC | GAA | GAA | GTT | TCT | GAA | AAA | GAA | CTT | ATG | GAA | GTA | |
|---|---|---|---|---|---|---|---|---|---|---|---|---|---|---|
| | Ala | Ile | Glu | Glu | Val | Ser | Glu | Lys | Glu | Leu | Met | Glu | Val | 26 |
| | | | | | | | -10 | | | | | | | |

| 80 | GCT | GGT | GGT | AAA | AGA | GGT | ACA | GGT | TGG | TTT | GCA | ACT | ATT | |
|---|---|---|---|---|---|---|---|---|---|---|---|---|---|---|
| | Ala | Gly | Gly | Lys | Arg | Gly | Thr | Gly | Trp | Phe | Ala | Thr | Ile | 39 |
| | | | -1 ↑ +1 | | | | | | | | | | +10 | |

| 120 | ACT | GAT | GAC | TGT | CCA | AAC | TCA | GTA | TTC | GTT | TGT | TGT | TAA | |
|---|---|---|---|---|---|---|---|---|---|---|---|---|---|---|
| | Thr | Asp | Asp | Cys | Pro | Asn | Ser | Val | Phe | Val | Cys | Cys | • | 52 |
| | | | | | | | | | | +20 | | | | |

Figure 3

SEQUENCE LISTING

```
<160> NUMBER OF SEQ ID NOS: 7

<210> SEQ ID NO 1
<211> LENGTH: 6
<212> TYPE: PRT
<213> ORGANISM: Streptococcus salivarius

<400> SEQUENCE: 1

Gly Gly Gly Val Ile Gln
1               5

<210> SEQ ID NO 2
<211> LENGTH: 111
<212> TYPE: DNA
<213> ORGANISM: Streptococcus salivarius
<220> FEATURE:
<221> NAME/KEY: CDS
<222> LOCATION: (37)..(111)

<400> SEQUENCE: 2
ttgactcttg aagaacttga taacgttctt ggtgct ggt ggt gga gta atc caa        54
                                        Gly Gly Gly Val Ile Gln
                                          1               5 acc att tca cac gaa tgt cgt atg aac tca tgg cag ttc ttg ttt act       102
Thr Ile Ser His Glu Cys Arg Met Asn Ser Trp Gln Phe Leu Phe Thr
             10                  15                  20 tgt tgc tct                                                           111
Cys Cys Ser
        25

<210> SEQ ID NO 3
<211> LENGTH: 25
<212> TYPE: PRT
<213> ORGANISM: Streptococcus salivarius

<400> SEQUENCE: 3

Gly Gly Gly Val Ile Gln Thr Ile Ser His Glu Cys Arg Met Asn Ser
1               5                  10                  15

Trp Gln Phe Leu Phe Thr Cys Cys Ser
            20                  25

<210> SEQ ID NO 4
<211> LENGTH: 153
<212> TYPE: DNA
<213> ORGANISM: Streptococcus salivarius
<220> FEATURE:
<221> NAME/KEY: CDS
<222> LOCATION: (88)..(153)

<400> SEQUENCE: 4
atgattgcca tgaaaaactc aaaagatatt ttgaacaatg ctatcgaaga agtttctgaa       60
aaagaactta tggaagtagc tggtggt aaa aga ggt aca ggt tgg ttt gca act      114
                        Lys Arg Gly Thr Gly Trp Phe Ala Thr
                         1               5
```

-continued

```
att act gat gac tgt cca aac tca gta ttc gtt tgt tgt                    153
Ile Thr Asp Asp Cys Pro Asn Ser Val Phe Val Cys Cys
10              15                  20
```

<210> SEQ ID NO 5
<211> LENGTH: 22
<212> TYPE: PRT
<213> ORGANISM: Streptococcus salivarius

<400> SEQUENCE: 5

```
Lys Arg Gly Thr Gly Trp Phe Ala Thr Ile Thr Asp Asp Cys Pro Asn
1               5                   10                  15

Ser Val Phe Val Cys Cys
            20
```

<210> SEQ ID NO 6
<211> LENGTH: 7
<212> TYPE: PRT
<213> ORGANISM: Streptococcus salivarius
<220> FEATURE:
<223> OTHER INFORMATION: corresponding probe sequence

<400> SEQUENCE: 6

```
Ser Trp Gln Phe Leu Phe Thr
1               5
```

<210> SEQ ID NO 7
<211> LENGTH: 21
<212> TYPE: DNA
<213> ORGANISM: Artificial Sequence
<220> FEATURE:
<223> OTHER INFORMATION: probe sequence
<221> NAME/KEY: misc_feature
<222> LOCATION: (1)..(21)
<223> OTHER INFORMATION: 'n' can be any nucleotide 'a','g','c' or 't';
      and 'r' can be either 'a' or 'g'

<400> SEQUENCE: 7
tcntggcaat ttttrtttac t                                                 21

LANTIBIOTIC

This invention relates to lantibiotics, organisms producing such lantibiotics, and to the uses of both the organisms and lantibiotics produced therefrom.

BACKGROUND

Bacterial infection in humans is a problem of both considerable personal concern, and economic importance in the heath field.

Streptococcal infections are particularly prevalent causing ailments ranging from dental caries and minor throat infections to serious diseases such as scarlet fever, rheumatic fever and acute glomerulonephritis.

In order to reduce the incidence of streptococcal infections, it is desirable to control or prevent the growth of the harmful causative bacteria. One approach towards this is to provide bacteriocins and like substances (including lantibiotics) active against streptococci and organisms capable of producing such substances, which are suitable for use in controlling or preventing the growth of harmful streptococci bacteria.

A number of bacteriocins are known. Examples of bacteriocins derived from gram positive bacteria are given in Tagg et al, (1976), *Bacteriol Rev.* Vol. 40, pp 722–756. Further examples of such bacteriocins are lacticin 481 from *Lactobacillus lactis* (Piard et al, (1992), *Applied and Environmental Microbiology*, Vol. 58, pp 279–284), variacin from *Micrococcus varians* (U.S. Pat. No. 5,981,261) and the bacteriocins from *Streptococcus thermophilus* described in EP 0643136.

*Streptococcus salivarius* has also long been known to have a high incidence of lantibiotic production (Dempster RP et al (1982) *Arch Oral Biol* 27:151). One lantibiotic which has been characterised from *S. salivarius* is salivaricin A (Ross et al (1993) *Appi Envir Microbiol* 59:2014). However, while demonstrating inhibitory activity against a number of streptococcal species, the activity was bacteriostatic rather than bactericidal. Salivaricin A and microorganisms which produce it therefore do not provide a complete answer to controlling streptococcal infections.

The applicants have now identified a further antibacterial protein from *S. salivarius* This protein, which the applicants have found to have bacteriocidal efficacy rather than being simply bacteriostatic, is the primary focus of the present invention.

SUMMARY OF THE INVENTION

Accordingly, in one aspect, the present invention may broadly be said to consist in an antibacterial protein which can be isolated from *S. salivarius* strains K12 and K30, which has a molecular mass of approximately 2733 Da as determined by ion-spray mass spectrometry, and the N-terminal amino acid sequence Gly-Gly-Gly-Val-Ile-Gln, or an antibacterial fragment or variant thereof which has greater than 80% amino acid sequence homology with the protein.

The protein of the invention has been termed by the applicants "salivaricin B", with the full nucleotide and amino acid sequences being given in FIG. 2, together with the sequences of a portion of the leader peptide.

Conveniently, salivaricin B is obtained by expression of a DNA sequence coding therefor in a host cell or by cult g producer strains *S. salivarius* K12 or K30.

In a further aspect, the invention provides an antibacterial composition which includes a protein as defined above or an organism which can express a protein as defined above.

In still a further aspect, the invention provides a therapeutic formulation comprising salivaricin B as defined above or an antibacterial fragment or variant thereof in combination with a diluent, carrier and/or excipient.

In yet a further aspect, the invention provides a therapeutic formulation comprising an organism capable of expressing salivaricin B as defined above, or an antibacterial fragment or variant thereof, in combination with a diluent, carrier and/or excipient.

Preferably, said organism is capable of expressing salivaricin B alone or in combination with a secondary antibacterial agent.

More preferably, said secondary antibacterial agent is a BLIS; most preferably salivaricin A2. The full nucleotide and amino acid sequences for Salivaricin A2 are given in FIG. 3, together with the sequences of the leader peptide.

Conveniently, said organism is selected from *S. salivarius* strains K12 and K30.

In a particularly preferred embodiment, the therapeutic formulations are in the form of foods or drinks, most preferably in the form of dairy product-based foods or drinks.

Alternative forms are medicaments and confectioneries.

In still a further aspect, the invention provides an organism which expresses salivaricin B.

Preferably, said organism is selected from *S. salivarius* strains K12 and K30.

In still further aspects of the invention, there are provided methods of treating an individual to at least inhibit growth of harmful streptococcal bacteria in the upper respiratory tract comprising the step of administering an effective amount of salivaricin B orally to said individual.

Preferably, said salivaricin B is administered as part of a therapeutic composition.

Conveniently, m said method said inhibitory effect is caused by colonising at least part of the upper respiratory tract of an individual with a viable non-pathogenic organism which expresses salivaricin B.

Preferably, said organism is administered as part of a food or drink.

More preferably, said organism is a *S. salivarius* strain selected from strains K12 and K30.

In yet a further embodiment, said method includes a preliminary step of pre-treating said individual to at least reduce the bacterial population present in the upper respiratory tract.

Preferably, said pre-treatment comprises the step of administering an antibiotic, preferably erythromycin, orally to said individual.

In yet a further embodiment, the invention provides a method of treatment of a patient against infections of the upper respiratory tract caused by Streptococcal organisms which comprises the steps of:

(i) orally administering to said patient an amount of an antibiotic effective to reduce the numbers of streptococci present; and (ii) administering, to the resulting bacterially depopulated environment, BLIS producing *S. salivarius* organism(s) to repopulate said environment Although the invention is broadly as described above, it will be appreciated by those persons skilled in the art that the invention is not limited thereto but also includes embodiments of which the following description gives examples, together with the aspects fully defined in the appended claim set.

DESCRIPTION OF THE DRAWINGS

Reference can be made to the accompanying drawings in which:

FIG. 2 shows the nucleotide and amino acid sequence for salivaricin B, including part of the leader peptide; and FIG. 3 shows the nucleotide and amino acid sequence for salivaricin A2, inclusive of the leader peptide.

Figure 1:
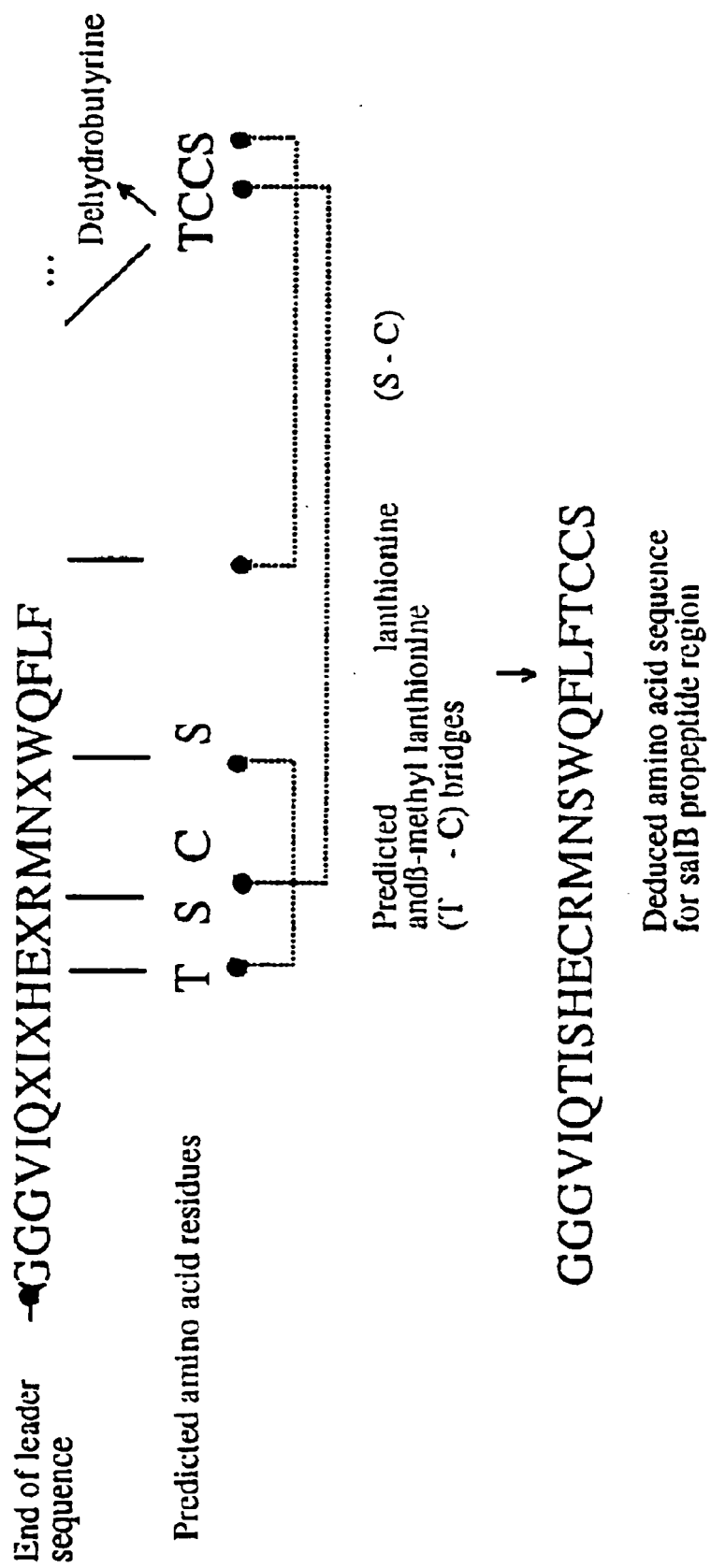
FIG. 1 shows the structural features of salivaricin B.

SEQ ID NOs: are assigned as follows:

SEQ ID NO: 1 refers to the N-terminal sequence of salivaricin B;

SEQ ID NO: 2 refers to the nucleotide sequence for salivaricin B;

SEQ ID NO: 3 refers to the amino acid sequence for salivaricin B including part of the leader peptide;

SEQ ID NO: 4 refers to the nucleotide sequence for salivaricin A2;

SEQ ID NO: 5 refers to the amino acid sequence for salivaricin A2 inclusive of the leader peptide;

SEQ ID NO: 6 refers to the amino acid sequence corresponding to the probe sequence.

SEQ ID NO: 7 refers to the nucleotide sequence corresponding to the probe sequence.

DESCRIPTION OF THE INVENTION

BLIS (bacteriocin-like inhibitory substances) are extracellularly released bacterial peptides or proteins that in low concentrations are able to kill certain other closely related bacteria by a mechanism against which the producer cell exhibits a degree of specific immunity.

The term lantibiotic is a term derived from lanthionine-containing antibiotics (Schnell et al Nature 333:276, 1988). Lantiobiotics are a category of BLIS. The lantibiotics are ribosomally synthesised as prelantibiotics, having an N-terminal extension (leader peptide) that is cleaved off by a processing enzyme during formation of the mature (biologically active form) of the molecule. A characteristic feature is that they are polycyclic polypeptides containing lanthionine and/or β-methyl lanthionine, which form thio-ether bridges within the peptide chain. A classification of the currently reported lantibiotics into two types, A and B, has been proposed by Jung in *Angewandte Chemie* 30:1051–1192, 1991.

Previous investigations by the applicant located a number of BLIS-producing strains of *Streptococcus salivarius* with activity against certain other streptococci. The BLIS produced by one strain (strain 20P3) was isolated, partially purified and a preliminary characterisation effected. This preliminary characterisation indicated that the BLIS produced was a relatively heat stable protein of molecular mass in the range 3500 to 8000 Da. The BLIS was given the name SAL 20P3.

Subsequent investigations elicited the amino acid sequence of SAL 20P3, together with its molecular mass. The specifically identified lantibiotic was renamed salivaricin A (Ross et al, Appl. Envir. Microbiol 59:2014).

The BLIS of the present invention is distinct from salivaricin A. This distinction is both in terms of its molecular mass (2733 Da compared with 2316 Da for salivaricin A) and in terms of its amino acid sequence as shown in FIG. 2. Salivaricins A and B are also distinct in terms of their inhibitory activity. Specifically, whereas salivaricin A has been found to be effective as a bacteriostat against most strains of *Streptococcus pyogenes*, salivaricin B has been determined to be bacteriocidal. More importantly, no strains of *S. pyogenes* that are resistant to salivaricin B have yet been detected.

Salivaricin B is expressed by *S. salivarius* strains K12 and K30. *S. salivarius* strains K12 and K30 were deposited with Deutsche Sammlung von Mikroorganismen Und Zellkulturen GmbH, Mascheroder Weg 1 b, D-38124 Braunschweig, Germany on 8 Oct. 1999. Strain K12 has been assigned accession number DSM 13084, whereas strain K30 has been assigned accession number DSM 13085.

Therefore, in a first aspect, the invention is directed to the antibacterial protein, salivaricin B. The invention also provides fragments or variants of salivaricin B where they exhibit functional equivalency.

It will be further appreciated that modifications an be made to the native amino acid sequence of both the protein and active fragments thereof while still at least substantially retaining their biological activity. Such modifications to the native amino acid sequence to result in the insertion, substitution or deletion of one, two or three amino acids are specifically within the scope of this invention, provided that the variant proteins have or include a sequence which is greater than 80% homologous with the amino acid sequence of native salivaricin B.

It will of course be understood that a variety of substitutions of amino acids is possible while still achieving this. Conservative substitutions are described in the patent literature, as for example, in U.S. Pat. Nos. 5,264,558 or 5,487,983. It is thus expected, for example, that interchange among non-polar aliphatic neutral amino acids, glycine, amine, proline, valine and isoleucine, would possibly be made. Likewise, substitutions among the polar aliphatic neutral amino acids, serine, threonine, methionine, asparagine and glutamine could possible be made. Substitutions among the charged acidic amino acids, aspartic acid and glutamic acid, could probably be made, as could substitutions among the charges basic amino acids, lysine and arginine. Substitutions among the aromatic amino acids, including phenylalanine, histidine, tryptophan and tyrosine would also likely be possible. These sorts of substitutions and interchanges are well known to those skilled in the art. Other substitutions might well be possible. Of course, it would also be expected that the more the percentage of homology ie. sequence sarity, of a variant protein with a naturally occurring protein exceeds the 80% threshold, the greater the retention of activity.

The protein and fragments of the invention can be prepared in a variety of ways. For example, by isolation from a natural source (such as *S. salivarius* strains K12 and/or K30), by synthesis using any suitable known techniques (such as is described for nisin synthesis by Wakamiya et al., (1991) in "Nisin and Novel Lantibiotics" ed. G. Jung and H. G Shal, 189–203, Escom, Leiden or by solid phase synthesis as described by Merrifield (1964) *J. Am. Chem. Assoc.* 85, 2149–2154, or by synthesis in homogeneous solution as described by Houbenwycl (1987), Methods of Organic Chemistry, Vol I and II) or through employing recombinant DNA techniques such as described by Sambrook et al (1989), Molecular cloning: A Laboratory Manual, Cold Spring Harbour Press, New York, USA The variants of both the native protein and its active fragments can similarly be made by any of those techniques known in the art. For example, variants can be prepared by site-specific mutagenesis of the DNA encoding the native amino acid sequence as described by Adelman et al, DNA 2, 183 (1983).

Where recombinant methodology is used to produce the BLIS, it is necessary as a first step to obtain DNA encoding the desired product. Such DNA also comprises an aspect of this invention.

The nucleotide sequence of a polynucleotide encoding salivaricin B is shown in FIG. 2.

The DNA of the invention may encode the native protein or an active fragment thereof.

The DNA can be isolated from, for example, *S. salivarius* strains K12 and K30 using probes and/or amplification primers based upon the determined nucleotide sequence of salivaricin B. The DNA thus identified may be produced as intron free cDNA using conventional techniques. The DNA can also be produced in the form of synthetic oligonucleotides where the size of the active frogments permits, for example by using the phosphotriester method of Matteucci et al J. Am. Chem. Soc. 103:3185–3191, 1981. Still further, the DNA can be produced using an appropriate commercially available DNA synthesiser, such as the Applied BioSystems DNA synthesiser.

The invention also contemplates variants of the protein and its fragments which differ from the native amino acid sequences by the insertion, substitution or deletion of one or more amino acids. Where such a variant is desired, the nucleotide sequence of the native DNA is altered appropriately. This alteration may be made through elective synthesis of the DNA or by modification of the native DNA by, for example, site-specific or cassette mutagenesis.

Preferably, where portions of cDNA or genomic DNA require sequence modifications, site-specific primer directed mutagenesis is employed. This technique is now standard in the art.

Once obtained, the modified DNA is treated to be suitable for insertion into the appropriate cloning and/or expression vector. To this end the DNA is cleaved, tailored and religated as required.

Cleavage is performed by treatment with restriction enzymes in a suitable buffer. Any of the large number of commercially available restriction enzymes can be used in the manner specified by the manufacturer. After cleavage, the nucleic acid is recovered by, for example, precipitation with ethanol.

Tailoring of the cleaved DNA is performed using conventional techniques. For example, if blunt ends are required, the DNA may be treated with DNA polymerase 1 (Klenow), phenol and chloroform extracted, and precipitated by ethanol.

Religation can be performed by providing approximately equimolar amounts of the desired components, appropriately tailored for correct matching, and treatment with an appropriate ligase (e.g. $T_4$ DNA ligase).

The DNA molecule thus obtained is inserted into a cloning vector at a location which permits the protein product for which it codes to be expressed.

Suitable cloning vectors may be constructed according to well known techniques, or may be selected from the large number of cloning vectors available in the art. While this cloning vector selected may vary according to the host cell intended to be used for expressing the BLIS-encoding DNA, useful cloning vectors will generally have the following characteristics:

(i) the ability to self-replicate;

(ii) possession of a single target for any particular restriction endonuclease; and (iii) desirably, carry genes for a readily selectable marker such as antibiotic resistance.

Two major types of cloning vectors possessing the aforementioned characteristics are plasmids and bacterial viruses (bacteriophages or phages). Examples of suitable cloning vectors include pUC18, Mp18, Mp19, pRB322, pMB9, ColE1, and pCR1 from *E. coli*; wide host range plamids including RP4, phage DNA's, such as lambda and M13 and shuttle vectors such as pSA3 and pAT28.

For expression of the BLIS-encoding DNA in the host, the cloning vector must also incorporate an expression control sequence. A typical expression control sequence can be described in terms of five elements. In the order in which they appear in the gene, the elements are as follows:

(a) the promoter region;

(b) the 5' untranslated region (signal or leader sequence);

(c) the protein coding sequence;

(d) the 3' untranslated region; and (e) the transcription termination region.

The function of each of these elements is well recognised. Any of a wide range of such control sequences can be used including, for example, those from the lipoprotein gene, the β-galactosidase gene, the tryptophan gene, the β-lactamase gene, and phage lambda.

As element (c), the DNA sequence coding for the lantibiotic is inserted into the cloning vector control sequence in the manner indicated above.

An appropriate host into which the cloning vector is to be inserted is then selected. Potentially useful hosts include bacteria, yeasts, fungi, insect, animal and plant cells. Procaryotic hosts are generally preferred for the present invention. Non-disease causing bacterial hosts are particularly suitable.

Bacterial hosts are generally selected from among the gram positive bacteria. Streptococcus hosts are preferred for use in the present invention.

As win be appreciated, in the selected host system, plasmid vectors that contain replication sites and control sequences derived from a species compatible with the host are used.

The cloning vector formed as above is used to transform the selected host, again using techniques well known in the art, for example, the calcium chloride treatment as described by Cohen, S. N. Proc. Nat. Acad. Sci. 69, 2110, 1972.

Upon transformation of the selected host with the cloning vector, the protein or fragment encoded can be produced, potentially as a fusion protein, by culturing the host cells. The exogenous protein product or fragment is then isolated using routine methods including ammonium sulfate precipitation, column chromatography (eg. ion exchange, gel filtration, affinity chromatography, etc.) electrophoresis, and ultimately, crystallisation (see generally "Enzyme Purification and Related Techniques". *Methods in Enzymology*, 22, 233–577 (1971)). Purification is effected as necessary using conventional techniques.

Where recombinant methodology is employed, the DNA of the invention may also code for a fusion protein comprising the antibacterial protein or fragment and a vector protein to assist with isolation and purification. Generally, this vector protein may be cleaved chemically or enzymatically from the antibacterial protein or fragment according to known techniques.

A specific chimeric form of protein could also have application. A DNA sequence encoding each entire protein, or a portion of the protein, could be linked, for example, with a sequence coding for another BLIS such as salivaricin A2 so that expression of the DNA sequence produces a chimeric protein with an expanded spectrum of antibacterial activity.

Once purified the protein is then available for use. Such uses include as general antibacterial agents (eg. as preservative in foods) as well as therapeutically. In this context, it will be appreciated that "therapeutically" includes prophylactic treatment.

Therefore, in a further aspect, the present invention is directed to therapeutic formulations suitable for use in the treatment or prevention of microbial infections, particularly streptococcal infections. The formulations are particularly suitable for use against *S. pyogenes* and *S. sobrinus*. These therapeutic formulations comprise salivaricin B or a fragment or variant thereof in combination with a diluent, carrier or excipient therefor, such as are known in the art. Examples of therapeutic formulations in which salivaricin B can be employed include are orally administrable medicaments such as capsules, lozenges, syrups, mouthwashes, gargles, toothpastes, and mouth sprays but are not limited thereto. Further examples include topically administrable formulations such as moisturising creams and cosmetics to combat bacterial growth on the skin.

In a further aspect the present invention provides a therapeutic formulation comprising a non-disease-causing viable organism capable of colonising the upper respiratory tract or a part thereof and expressing the lantibiotic of the invention, in combination with a carrier, diluent and/or excipient.

In one embodiment the organism is a transformed host organism produced in accordance with the invention. It is, however, preferred that the organism be one which produces salivaricin B as a native product. Examples of such organisms are *S. salivarius* strains K12 and K30.

*S. salivarius* strains K12 and K30 have been determined as expressing not only salivaricin B but also salivaricin A2. Salivaricin A2 is related but not identical to salivaricin A. The full sequences (polynucleotide and amino acid) for salivaricin A2 are shown in FIG. 3.

In this embodiment, it is preferred that the therapeutic formulations of the invention are in the form of a food, confectionery or drink. It is particularly preferred that the foodstuff or drink be a dairy product-based food or drink, including by way of example, yoghurt, cheese, milk, milk biscuits and flavoured milks. In the case of a confectionery, the therapeutic formulation can be a chewing gum such as a chewing gum as described in WO 00/05972.

A particularly preferred formulation is where freeze-dried strains of salivaricin B-producing S. salivarius be included in milk powder formulations in a manner similar to that previously reported for the preparation of Bifidus Milk Powder (Nagawa et al (1988); J Dairy Sci 71:1777–1782).

Various aspects of the invention will now be illustrated in a non-limiting way by reference to the following experimental section.

Experimental

Extraction of Salivaricin

Salivaricin B was purified from lawn cultures of the test strains *S. salivarius* K12 and K30 grown for 18 hours at 37° C. in a 5% carbon dioxide in air atmosphere on M17 medium supplemented with 0.5% Davis agar, 0.5% sucrose, 0.5% human plasma and 0.1% calcium carbonate. The lawn cultures were inoculated by swabbing on to the surface of the agar medium from an 18 hour 37° C. Todd Hewitt broth culture of the producer strain. Extraction of the salivaricin B activity is achieved by freezing the agar plates at −70° C. and then thawing at room temperature to collapse the agar gel, followed by centrifugation to clarify the extracted liquor. The titre of inhibitory activity in these freeze/thaw extracts is generally 2–4 AU/ml.

Titration of Salivaricin Activity

Salivaricin activity is titrated using an agar surface assay. Drops (20 ul) of two-fold saline dilutions of the sample are assayed against *Microoccus luteus* T-18 on Columbia agar base. The reciprocal of the highest dilution to produce a definite zone of inhibition of the growth of the indicator lawn is the titre in arbitrary units per ml (Au/ml) of salivaricin activity.

Purification of Salivaricin B

A two-litre volume of freeze thaw extract was applied to an XAD-2 column (diameter 5.0 cm, bed volume 150 ml; Serva) and washed with 7 bed volumes of 50% (v/v) methanol. Salivaricin activity was eluted with 5 bed volumes of 90% (v/v) methanol (adjusted to pH2 with 11.6 M CH1) and concentrated by evaporation at 50° C. under reduced pressure. Aliquots (1-ml) of this material were applied to a Brownlee C8 reverse phase column (Aquapore RP 300; pore size, 7um; 30 by 4.6 mm; Applied Biosystems, Inc.), equilibrated with 0.1% trifluoroacetic acid TFA). Fractionation of this material is achieved by using a Pharmacia fast protein liquid chromatography (FPLC) system at a flow rate of one ml per minute using a 10 minute gradient (0 to 28% acetonitrile containing 0.085% TFA) followed by 80 minute isocratic (28% acetonitrile) elution. During this isocratic elution, phase separation is achieved of salivaricin A (elution starting at around 40 minutes) and salivaricin B (starting at around 60 minutes). Each 1-ml fraction was tested for inhibitory activity against *M.luteus* T18. The active fractions in each region corresponding to salivaricin A and salivaricin B were separately pooled as partially purified preparations of the bacteriocins. Each pool was lyophilized and then dissolved in 0.1% TFA Aliquots of each of these preparations were then loaded onto a $C_{18}$ reversed-phase High Pressure Liquid Chromatography (HPLC) column (Alltech Nucleosil $C_{18;\ 10}$ um; 250.0×4.6 mm) equilibrated with 0.1% TFA and further fractionated using a Waters/Millipore HPLC system by application of appropriate gradients of acetonitrile.

Salivaricin A2 was eluted as a homogeneous peak with 34–35% acetonitrile and salivaricin B with 38–40% acetonitrile. Absorbence was monitored at 214 mm and fractions corresponding to the various peaks were collected manually. Inhibitory activity was detected by a spot diffusion teat using *M. luteus* T-18 as the indicator. The active fractions from each run were pooled, lyophilised and redissolved in 1 ml of Milli Q™-purified water containing 0.1% TFA. The fractions containing inhibitory activity (purified salivaricin) were pooled and stored at −20° C.

Ion-spray mass spectrometry indicated that the molecular mass of salivaricin B was 2733 Da. Edman analysis of purified salivaricin B revealed the N-terminal sequence Gly-Gly-Gly-Val-Ile-Gln.

Cloning of Salivaricin B

The amino acid sequence derived by purification and sequencing of the peptide enabled design of degenerate oligonucleotide DNA probes based upon the universal codon usage. The specific probe used (CF481) was based upon the amino acid sequence: S W Q F L F T. The corresponding nucleotide sequence was TCNTGGCAATTTTTTTRTT-TACT.

Chromosomal DNA was isolated from the *Streptococcus salivarius* strain, Min 5 by the method of Spanier and Cleary (1983). (Virology 130:514–522). A digest using both EcoR1 and HindIII restriction enzymes was done, and then the cut DNA was separated in a 1% agarose gel run at 40 V/cm for 18 hours (Sambrook et al. Molecular Cloning: A Laboratory Manual. 1989). The DNA was transferred to nylon membrane by Southern blotting following the instructions for use of Hybond-N+ (Amersham Pharmacia). Probe CF481 was labelled with gamma $P^{32}$ ATP using T4 polynucleotide kinase. Hybridisation with probe CF481 was carried out in a hybridisation tube at 38° C. for 18 hours. The membrane was washed twice for 5 minutes in 5×SSC, 0.5% SDS, and then twice for 20 minutes in 2×SSC, 0.20% SDS. The membrane was then exposed to X-ray film at −70° C. for 18 hours.

The area of the gel which corresponded to the hybridisation site of CF481 on the Southern blot was cut from the gel and the DNA extracted using a Qiagen QIAquick Gel Extraction Kit. For ligation, 1 μl of the vector pUC 19 which had been cut with the restriction enzymes EcoR1 and HindIII, was mixed with 15 μl of the cleaned Min5 DNA fragments, 2 μl ligation buffer, and 1 μl T4 DNA ligase (Roche). Incubation was for 18 hours at 15° C.

*E. coli* strain DH10β was used for transformation by electroporation with the ligated pUC 19. The transf rmed cells were grown for 1 hour in 1 ml of Luria Broth, and then plated onto Luria Broth agar with added ampicillin (100 μl/ml) and X-gal 20 mg/ml. After an overnight incubation at 37° C., white colonies were selected, subcultured and screened with the CF481 probe. Screening was carried out by lysing the *E coli* colonies in a 5% SDS 10% glycerol solution at 65° C. for 30 minutes. The colonies were then run in an agarose gel, Southern blotted, and the membrane hybridized with the CF481 probe in the same manner as described above. Positive colonies were then grown in Luria Broth with 100 μl/ml Ampicillin for 18 hours at 37° C. with shaking. The pUC 19 plasmid was then extracted using QIAprep Spin Miniprep Kit (Qiagen) and sequenced using pUC 19 forward and reverse primers.

The results are shown in FIG. 2.

Antibacterial Activity of Salivaricin B

Part 1

Strains of *S. salivarius such as* 20P3 and 5 that produce salivaricin A (but not salivaricin B) inhibit all of 9 standard indicator bacteria other than indicator 3. This pattern of inhibition in code form is known as production (P) type 677. By contrast, strains K12 and K30 that produce both salivaricin A2 and salivaricin B inhibit the growth of all 9 standard indicators, activity referred to as P-type 777. The P-typing test involves first growing the test strain on blood agar as a diametric streak culture. After removing this growth, the agar surface is sterilizied with chloroform vapour, aired and the 9 standard indicator bacteria (including 4 strains of *Streptococcus pyogenes*) are cross-streaked across the line of the original test strain inoculum. Following incubation, interference with growth of the indicators in the vicinity of the original producer streak is taken as indicative of bacteriocin activity. In the case of strains 20P3 and 5 (producers of salivaricin A) the inhibitory activity can be shown to be bacteriostatic ie viable indicator cells can be recovered in large numbers from the inhibition zone by sampling with a swab and transferring the cells to a fresh (non-bacteriocin-containing) agar medium. By contrast, the effect of the P-type 777 strains (shown also to produce salivaricin B) is bactericidal against the standard indicators ie no viable cells can be recovered from the inhibition zone in deferred antagonism tests. Furthermore, tests using purified preparations of salivaricin A and salivaricin B (data not shown) have confirmed that the action against *S. pyogenes* of salivaricin A is bacteriostatic whereas that of salivaricin B is bactericidal.

Part 2

The inhibitory activity of the salivaricins was determined by measurement of the decrease with time in the number of colony-forming units (CFU) of a suspension of the sensitive indicator streptococcus (*Streptococcus pyogenes* strain FF22) after mixing the cells with a salivaricin preparation. Twice-washed cells from an exponential Todd Hewitt broth culture of the indicator streptococcus were resuspended in 0.067 M phosphate buffer (pH 6.5) to the original culture volume. Portions of partially purified salivaricin (titre 16 Au/ml) or of phosphate buffer (control) were then mixed with an equal volume of the washed cell suspension and incubation was continued at 37° C. Survivors were determined at intervals by plating suitable 10-fold dilutions (in cold Todd Hewitt broth) of the test and control mixtures on Columbia agar base and incubating at 37° C. for 24 h. Viable counts were expressed as the total number of CFU per ml.

It was found that preparations of partially purified salivaricin B of titre 16 were lethal for over 99% of the CFU of exponential Todd Hewitt broth cultures of *S. pyogenes* strain FF22 in 4 h at 37° C. By contrast the partially purified preparation of salivaricin A2 of titre 16 when tested using under the same conditions killed less than 10% of strain FF22 cells. Further tests of the inhibitory spectra of partially purified salivaricin A2 and salivaricin B preparations were done by using the agar surface assay described above. Drops (20 ul) of a preparation of titre 16 Ua/ml were spotted onto lawn cultures of the test strains that had been freshly inoculated by swabbing the surface of a Columbia agar base plate with a ¹⁄₁₀₀ dilution in saline of an 18 h Todd Hewitt broth culture of that strain. Production of a definite zone of inhibited test strain growth upon incubation of these plates at 37° C. for 18 h was taken to indicate sensitivity of that strain to the salivaricin.

The results are shown in Table 1.

TABLE 1

| Species | Inhibitory activity | | |
| --- | --- | --- | --- |
| | Number tested | Sensitive to Sal A2 | Sensitive to Sal B |
| Streptococcus pyogenes | 15 | 15 | 15 |
| Streptococcus equisimilis | 5 | 5 | 5 |
| Streptococcus agalactiae | 5 | 0 | 2 |
| Streptococcus pneumoniae | 4 | 1 | 2 |
| Streptococcus sanguis | 6 | 0 | 6 |
| Streptococcus mutans | 6 | 0 | 0 |
| Streptococcus sobrinus | 4 | 0 | 3 |
| Corynebacterium diphtheriae | 4 | 0 | 4 |
| Lactobacillus casei | 2 | 1 | 2 |
| Stomatococcus mucilagenosus | 4 | 0 | 3 |
| Staphylococcus aureus | 4 | 0 | 0 |
| Branhamella catarrhalis | 1 | 0 | 1 |
| Escherichia coli | 2 | 0 | 0 |

Industrial Application

The results above demonstrate the inhibitory and bacteriocidal effect of salivaricin B and organisms which produce this BLIS. Salivaricin B and/or organisms which produce it are therefore applicable in methods of treating individuals against the harmful effects of streptococcal infections in the upper respiratory tract, including the mouth. These methods include methods of treatment of conditions such as streptococcal sore throats (caused mainly by *S. pyogenes*) and dental caries (caused in part by *S. sobrinus*).

The presently preferred orally administrable formulations are blends of freeze-dried *S. salivarius* strains with slum milk powder or the like which has been flavoured to enhance palatability.

Indications to date are that such formulations are effective when reconstituted by addition of water and sipped on three to four occasions during the course of the day, such that a total of 50 mls of the flavoured product is consumed (containing approximately 2×10⁷ cells/ml of freeze-dried *S. salivarius* organism(s)).

Where the freeze-dried *S. salivarius* strains are selected from K12 and K30, there is the added advantage that salivaricin B is expressed together with salivaricin A2. Co-expression of these two BLIS renders the formulation particularly bacteriocidal in relation to *S. pyogenes* and *S. sobrinus*, as well as in relation to a number of other bacteria.

It will be appreciated that the above description is provided by way of example only and that variations in both the materials used and the techniques used which are known to those persons skilled in the art are contemplated. The scope of protection is limited only by the claims which follow.

What is claimed is:

1. An isolated antibacterial protein having the amino acid sequence of SEQ ID NO: 3.

2. The protein as claimed in claim 1, wherein the protein is bacteriocidal.

3. The protein as claimed in claim 2, wherein the protein is bacteriocidal with respect to *Streptococcus pyogenes*.

4. An antibacterial composition comprising the protein as claimed in claim 1 or a microorganism which expresses the protein as claimed in claim 1.

5. A formulation which comprises:
   (i) the protein as claimed in claim 1; or
   (ii) an organism which expresses the protein as claimed in claim 1,
in combination with a diluent, carrier and/or excipient.

6. The formulation as claimed in claim 5, which is an orally administrable medicament.

7. The formulation as claimed in claim 6, wherein the medicament is a syrup, mouthwash, gargle, toothpaste or mouth spray.

8. The formulation as claimed in claim 6, wherein the medicament is in a unit dosage form.

9. The formulation as claimed in claim 7, wherein the medicament is a lozenge or capsule.

10. The formulation as claimed in claim 5 in which said protein is included in a food or drink.

11. The formulation as claimed in claim 10 in which said food or drink is a dairy product based food or drink.

12. The formulation as claimed in claim 11 in which said protein is included in milk powder, milk biscuits, milk, yoghurt or cheese.

13. The formulation as claimed in claim 11 in which said protein is included in a flavoured milk.

14. The formulation as claimed in claim 5, in which said protein is included in a confectionery.

15. The formulation as claimed in claim 14 in which said confectionery is a chewing gum.

16. The formulation as claimed in claim 5, which further comprises one or more secondary antibacterial agents.

17. The formulation as claimed in claim 16 in which said secondary antibacterial agent(s) are selected from bacteriocin-like inhibitory substance(s) (BLIS).

18. The formulation as claimed in claim 15 which further comprises of Salivaricin A, a microorganism which expresses Salivaricin A, an antibacterial protein which has the amino acid sequence of SEQ ID NO:5, or microorganism which expresses the antibacterial protein which has the amino acid sequence of SEQ ID NO:5.

19. A microorganism, in substantially pure form, comprising a polynucleotide which:
   encodes the protein as claimed in claim 1.

20. The organism as claimed in claim 19 in which said polynucleotide is heterologous to the microorganism.

21. The organism as claimed in claim 19 which is a *Streptococcus salivarius* microorganism.

22. A biologically pure culture of *Streptococcus salivarius* strain K12 on deposit at Deutsche Sammlung von Mikroorganismen Und Zellkulturen GmbH, Braunschweig, Germany, accession number DSM 13084 wherein the *Streptococcus salivarius* comprises SEQ ID NO. 3.

23. A biologically pure culture of *Streptococcus salivarius* strain K30 on deposit at Deutsche Sammlung von Mikroorganismen Und Zellkulturen GmbH, Braunschweig, Germany, accession number DSM 130851 wherein the *Streptococcus salivarius* comprises SEQ ID NO. 3.

24. A formulation which includes *Streptococcus salivarius* strain K12 or *Streptococcus salivarius* strain K30 as identified in claim 22 or claim 23.

25. A method of treating an individual to reduce growth of harmful streptococcal bacteria in the upper respiratory tract, comprising the step of administering an effective amount of a protein as claimed in claim 1 orally to said individual.

* * * * *

UNITED STATES PATENT AND TRADEMARK OFFICE
CERTIFICATE OF CORRECTION

PATENT NO. : 6,773,912 B1
DATED : August 10, 2004
INVENTOR(S) : John Robert Tagg, Karen Patricia Dierksen and Matthew Upton It is certified that error appears in the above-identified patent and that said Letters Patent is hereby corrected as shown below:

<u>Column 13,</u>
Line 64, "7" should read -- 6 --.

Signed and Sealed this

Fourth Day of April, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,773,912 B1 | Page 1 of 1 |
| APPLICATION NO. | : 09/913763 | |
| DATED | : August 10, 2004 | |
| INVENTOR(S) | : John Robert Tagg, Karen Patricia Dierksen and Andrew Upton | |

It is certified that error appears in the above-identified patent and that said Letters Patent is hereby corrected as shown below:

On The Title page item (73) should read:

"University of Otago, Dunedin (NZ);" Bliss Technologies Limited, Dunedin (NZ)

Signed and Sealed this

Fifth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 6,773,912 B1  Page 1 of 1
APPLICATION NO. : 09/913763
DATED : August 10, 2004
INVENTOR(S) : John Robert Tagg, Karen Patricia Dierksen and Andrew Upton It is certified that error appears in the above-identified patent and that said Letters Patent is hereby corrected as shown below:

On The Title page item (73) should read:

"University of Otago, Dunedin (NZ);" Blis Technologies Limited, Dunedin (NZ)

This certificate supersedes the Certificate of Correction issued August 5, 2008.

Signed and Sealed this

Seventh Day of April, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,773,912 B1 | |
| APPLICATION NO. | : 09/913763 | |
| DATED | : August 10, 2004 | |
| INVENTOR(S) | : John Robert Tagg, Karen Patricia Dierksen and Andrew Upton | |

It is certified that error appears in the above-identified patent and that said Letters Patent is hereby corrected as shown below:

On The Title page item (73) should read:

-- Blis Technologies Limited, Dunedin (NZ) --

This certificate supersedes the Certificates of Correction issued August 5, 2008 and April 7, 2009.

Signed and Sealed this

Twenty-sixth Day of May, 2009

JOHN DOLL
*Acting Director of the United States Patent and Trademark Office*